United States Patent [19]

Wollenweber et al.

[11] Patent Number: 5,807,502
[45] Date of Patent: Sep. 15, 1998

[54] AQUEOUS FATTY ALCOHOL DISPERSIONS

[75] Inventors: Horst-Werner Wollenweber, Duesseldorf; Rainer Hoefer, Neuss; Heinz-Guenther Schulte, Muehlheim, all of Germany

[73] Assignee: Henkel Kommanditgesellschaft Auf Aktien, Duesseldorf, Germany

[21] Appl. No.: 765,752

[22] PCT Filed: Jun. 12, 1995

[86] PCT No.: PCT/EP95/02260

§ 371 Date: Dec. 20, 1996

§ 102(e) Date: Dec. 20, 1996

[87] PCT Pub. No.: WO95/35143

PCT Pub. Date: Dec. 28, 1995

[30] Foreign Application Priority Data

Jun. 20, 1994 [DE] Germany .......................... 44 21 270.4

[51] Int. Cl.⁶ .................................................. B01D 19/04
[52] U.S. Cl. ........................... 252/321; 252/358; 252/312
[58] Field of Search .................... 252/321, 358, 252/312

[56] References Cited

U.S. PATENT DOCUMENTS

| | | | |
|---|---|---|---|
| 3,226,295 | 12/1965 | Goetz et al. | 252/358 |
| 3,406,208 | 10/1968 | Blaser et al. | 568/623 |
| 3,779,934 | 12/1973 | Altenschopfer et al. | 252/351 |
| 3,892,522 | 7/1975 | Schade et al. | 8/137 |
| 4,009,119 | 2/1977 | Poschmann et al. | 252/358 |
| 4,234,444 | 11/1980 | Wegener et al. | 273/403 |
| 4,303,549 | 12/1981 | Boylan | 252/321 |
| 4,338,212 | 7/1982 | Wegener et al. | 510/413 |
| 4,340,500 | 7/1982 | Boylan | 252/321 |
| 4,396,524 | 8/1983 | Hempel et al. | 252/321 |
| 4,549,002 | 10/1985 | Hoefer et al. | 526/209 |
| 4,600,523 | 7/1986 | Priorr et al. | 252/321 |
| 4,976,888 | 12/1990 | De Clercq et al. | 252/358 |
| 5,147,412 | 9/1992 | Klinksiek et al. | 23/293 R |
| 5,346,973 | 9/1994 | Feustel et al. | 526/209 |

FOREIGN PATENT DOCUMENTS

| | | |
|---|---|---|
| 1 297 755 | 3/1992 | Canada . |
| 230 977 | 8/1987 | European Pat. Off. . |
| 399 266 | 11/1990 | European Pat. Off. . |
| 11 90 927 | 4/1965 | Germany . |
| 29 00 030 | 7/1980 | Germany . |
| 30 39 393 | 4/1981 | Germany . |
| 30 01 387 | 7/1981 | Germany . |
| 36 01 929 | 7/1987 | Germany . |
| 40 06 391 | 9/1991 | Germany . |

OTHER PUBLICATIONS

Database WPI, Week 8323 London: Derwent Publications Ltd., AN–83–55096K, Class A97, JP58–072000 A (Daiichi Kogyo Seiyaku), abstract.

*Primary Examiner*—Richard D. Lovering
*Assistant Examiner*—Daniel S. Metzmaier
*Attorney, Agent, or Firm*—Ernest G. Szoke; Wayne C. Jaeschke; Real J. Grandmaison

[57] ABSTRACT

An aqueous fatty alcohol dispersion containing:

(a) 5% to 40% by weight of a $C_{10}$–$C_{28}$ fatty alcohol;
(b) 0.5% to 5% by weight of anionic interfacially active compounds;
(c) 0.5% to 5% by weight of nonionic interfacially active compounds comprising the reaction products of ethylene oxide with alkane-1,2-diols containing 6 to 18 carbon atoms, and
(d) the balance, water. The dispersion is useful as an antifoam agent.

16 Claims, No Drawings

AQUEOUS FATTY ALCOHOL DISPERSIONS

This application is filed under 35 U.S.C. § 371 and is based on PCT/EP95/02260, filed Jun. 12, 1995.

BACKGROUND OF THE INVENTION

1. Field of the Invention

This invention relates to aqueous fatty alcohol dispersions and to their use as antifoam agents, preferably in the paper industry, in the wastewater sector, in the building industry and in the production of waterborne paints and also to their use as an additive for dispersion-bonded plasters.

The generation of foam associated with the presence or with the use of surface-active substances is a serious problem in a number of industrial processes. Thus, in the production of paints and lacquers for example, intensive foaming occurs during grinding of the lacquer through the stirring in of air. This foaming makes the production of paints or lacquers more laborious because the plant can only be filled and operated with a fraction of the available volume. At the same time, however, foaming can also occur when the user wants to apply paints or lacquers to substrates. Small air bubbles can form and represent not only visible surface defects, but also weak spots in the dried film because they can easily burst under impact.

Problematical foams are also formed in papermaking on account of the air introduced into the water circuit. For example, foam stains can occur on the paper when foam passes onto the paper web during the sheet forming process. The increasing speeds at which papermaking machinery is operated increase the overall danger of air being mixed into the fiber suspension which can adversely affect the drainage of the paper stock on the papermaking machine and, ultimately, can lead to porous structures of the paper sheets. These basically known disadvantages are increased by the new papermaking machines with closed water circuits because foam-forming and foam-stabilizing substances accumulate in the closed systems. As the foregoing observations suggest, there is a considerable need in the industry both for defoamers which are capable of reducing foam which has already formed and for foam inhibitors which are intended to suppress the generation of foam. In addition, antifoam agents are also intended to drive air bubbles dissolved in liquid systems to the surface of those systems—a process which plays a major role as degassing or even as deaeration, for example in paints. Accordingly, antifoam agents in the context of the invention are intended both to reduce foam which has already formed and preventively to inhibit foaming and also to drive out air bubbles. These antifoam agents are expected to develop their effect quickly and durably in small quantities.

To solve the problems caused by foam in the building industry, there is a need for defoamers which are effective, do not cause any surface defects, do not undesirably sensitize the surfaces to water and—in gypsum boards for example—do not affect adhesion.

In the case of dispersion-bonded plasters, such as synthetic-resin- and silicate-bonded plasters, a long so-called open time is required for application to enable good grindability and the required plaster structures to be obtained. The high formulation-related percentage contents of additives and application to generally absorbent substrates result in a rapid release of the water present so that the open time is seriously limited. As soon as the setting process, i.e. drying, begins, the opportunity to structure or texture the surface is lost. At relatively high ambient temperatures in particular, the rapid release of water leads to a critical reduction in the open time of the dispersion-bonded plasters. Accordingly, there is a considerable need in the industry for additives which are capable of extending the open time of dispersion-bonded plasters.

2. Discussion of Related Art

Aqueous fatty alcohol dispersions are used in both fields of application. Thus, DE-A-36 01 929, for example, describes defoamers based on oil-in-water emulsions in which the oil phase of the emulsion contains a $C_{12-26}$ alcohol, a fatty acid ester and a hydrocarbon and interfacially active substances, for example sodium or ammonium salts of higher fatty acids, alkoxylated alkylphenols, ethoxylated unsaturated oils or sulfated ethoxylation products of nonylphenol or octylphenol, are used as the emulsifier.

DE-A-30 39 393 describes an aqueous antifoaming composition which contains water, at least one higher aliphatic alcohol, at least one solid fatty acid, at least one soap of a solid fatty acid and surface-active agents. The surface-active agents may be anionic and/or nonionic surfactants. The nonionic surfactants mentioned include ethylene oxide condensates in which at least one terminal group is terminated by condensation with an alcohol, alkylphenol or long-chain fatty acid.

The higher aliphatic alcohols present according to DE-A-36 01 929 and DE-A-30 39 393 are synthetic alcohols, so-called alfol alcohols, which are easier to disperse than natural fatty alcohols. In addition, ethoxylated alkylphenols are favored as nonionic surfactants in both these documents. Alkylphenol ethoxylates are toxicologically unsafe and, in addition, show poor biodegradability so that it would be better not to use compounds belonging to this class. Although, in overall terms, the anionic and/or nonionic surfactants proposed in the two documents in question are capable of stabilizing synthetic higher alcohols, they fail in the case of natural fatty alcohols, above all in cases where relatively high contents of natural fatty alcohol of more than about 20% by weight are required in the fatty alcohol dispersions. With natural fatty alcohol contents of this order, gelation or creaming occurs in the event of prolonged storage or in the event of storage at temperatures below 15° C., in many cases after only 1 day.

Accordingly, the problem addressed by the present invention was to provide aqueous fatty alcohol dispersions which would be stabilized with interfacially active compounds and which would be free from aromatic constituents and biologically degradable. In addition, the dispersions containing the difficult-to-disperse natural fatty alcohols would be stable in storage. This stability in storage would remain intact for longer periods than before, above all at temperatures below room temperature. In addition, the fatty alcohol dispersions would be easy to dose and would be usable and stable in storage over a broad temperature range. In cases where they are intended for use as antifoam agents, the aqueous fatty alcohol dispersions would additionally show high activity. When used in dispersion-bonded plasters, the aqueous fatty alcohol dispersions would be capable of extending the open time.

DESCRIPTION OF THE INVENTION

The requirements stated above are surprisingly satisfied by aqueous fatty alcohol dispersions which contain reaction products of ethylene oxide with alkane-1,2-diols containing 6 to 18 carbon atoms as nonionic interfacially active compounds.

Accordingly, the present invention relates to aqueous fatty alcohol dispersions containing $C_{10-28}$ fatty alcohols in the oil phase and
anionic interfacially active compounds and
nonionic interfacially active compounds and
water, characterized in that the nonionic interfacially active compounds are reaction products of ethylene oxide with alkane-1,2-diols containing 6 to 18 carbon atoms.

Preferred nonionic interfacially active compounds are those corresponding to general formula (I):

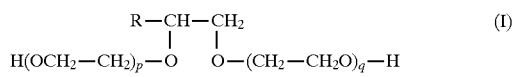

in which R is a saturated or unsaturated radical containing 6 to 18 carbon atoms attached via carbon and p and q are numbers of 0 to 50, the sum of p and q being in the range from 5 to 50.

Compounds corresponding to general formula (I) are already known as reaction products of ethylene oxide with aliphatic vicinal terminal alkanediols. DE-A-40 06 391 describes surfactant mixtures as emulsifiers for emulsion polymerization which contain reaction products of ethylene oxide with alkane-1,2-diols in addition to ethoxylated alcohols. In emulsion polymerization, surfactant mixtures of this type are required first for emulsification of the liquid monomers and later for their polymers. According to the present invention, the nonionic interfacially active compounds are mixed with anionic interfacially active compounds in order to be able to disperse the water-insoluble fatty alcohols. In addition, there is no reference in DE-A-0 06 391 to improved stability in storage.

The reaction products of ethylene oxide with alkane-1,2-diols may be prepared as described in DE-A40 06 391. Further relevant information can be found in DE-B-11 90 927, which describes the reaction of 1,2-diols containing 8 to 26 carbon atoms with ethylene oxide, and in DE-A-29 00 030 which describes a process for the ring opening of internal or terminal olefin epoxides containing 6 to 18 carbon atoms with polyhydric alcohols, such as ethylene glycol, and subsequent ethoxylation of the reaction products.

According to the invention, reaction products of ethylene oxide with saturated or unsaturated alkane-1,2-diols containing 6 to 18 carbon atoms are used as the compounds corresponding to general formula (I). Adducts of ethylene oxide with linear alkane-1,2-diols containing an odd or even number of carbon atoms or mixtures thereof are preferably used according to the invention as compounds corresponding to general formula (I). Ethoxylated alkane-1,2-diols containing 12 and/or 14 carbon atoms are most particularly suitable. They are produced in known manner from olefins and olefin mixtures containing terminal double bonds by epoxidation and subsequent catalytic ring opening of the resulting terminal epoxyalkanes with ethylene glycol. The ring opening of the 1,2-epoxyalkanes with ethylene glycol may be acid- or base-catalyzed. Where acids are used as catalysts, 1-hydroxy-2-(2-hydroxyethoxy)-2-alkanes containing two primary hydroxyl groups and 1-(2-hydroxyethoxy)-2-hydroxyalkanes containing one primary and one secondary hydroxyl group are formed in a ratio of about 50:50. In the case of the compounds containing two primary hydroxyl groups, the primary hydroxyl groups are capable of further reacting with ethylene oxide in substantially the same way. The compounds containing one primary and one secondary hydroxyl group show a preferred further reaction with ethylene oxide at the primary hydroxyl group. In addition, the ring opening of the 1,2-epoxyalkanes with an excess of ethylene glycol can be base-catalyzed. In this case, 1-(2-hydroxyethoxy)-2-hydroxyalkanes are essentially formed. Compounds corresponding to general formula (I) which have been prepared by acid-catalyzed ring opening of terminal epoxyalkanes with ethylene glycol and subsequent epoxidation are preferred for the purposes of the present invention.

The alkane-1,2-diols are converted into the compounds of general formula (I) by ethoxylation. The ethoxylation may be carried out by methods known from the prior art which lead to so-called narrow-range or broad-range products, depending on the choice of the alkoxylation catalyst. The choice of the alkoxylation catalyst influences the breadth of the spectrum of addition products, the so-called homolog distribution, of ethylene oxide with the alkane-1,2-diols. Thus, addition products with a broad homolog distribution are obtained in the presence of the catalytically active alkali metal alcoholates, such as sodium methylate, whereas an extremely narrow homolog distribution is obtained in the presence of hydrotalcite, for example, as catalyst.

Compounds corresponding to general formula (I) obtained by reaction of aliphatic alkane-1,2-diols with up to 49 moles of ethylene oxide per mole of alkanediol, the two hydroxyl groups of the alkane-1,2-diols optionally having been added by different quantities of ethylene oxide, are used for the purposes of the present invention. Accordingly, p and q independently of one another may represent a number of 0 to 50, with the proviso that the sum of p and q is a number of 5 to 50 and preferably a number of 5 to 30. So far as the indices p and q are concerned, it should be noted that this does not represent the entire degree of ethoxylation because the ethylene glycol used for ring opening also has to be taken into consideration.

The fatty alcohols present in the aqueous fatty alcohol dispersions preferably have melting points above 40° C. and, more particularly, above 50° C. The fatty alcohols may be synthetic and/or natural fatty alcohols. Saturated, linear and/or branched natural fatty alcohols containing 16 to 28 carbon atoms are preferred. Examples of the even-numbered fatty alcohols are palmityl, stearyl, arachidyl, behenyl, lignoceryl and ceryl alcohol and also 1-octacosanol.

As usual in oleochemistry, the even-numbered fatty alcohols may also be used in the form of the technical cuts obtained, for example, by hydrogenation from rapeseed oil rich in erucic acid, peanut oil, castor oil, beef tallow or fish oil, optionally after saturation of the unsaturated components. Apart from these natural fatty alcohols, saturated, linear synthetic fatty alcohols containing 16 to 28 carbon atoms obtainable by the Ziegler process, i.e. by oxidation of aluminium alkyls and subsequent hydrolysis, are also suitable for the purposes of the invention. Mixtures of even-numbered, linear fatty alcohols (alfols) are obtained in this way. Synthetic fatty alcohols obtained by the oxosynthesis, i.e. by reaction of olefin with carbon monoxide/hydrogen, such as odd-numbered alcohols, are also suitable for the purposes of the invention.

Saturated unbranched fatty alcohols containing 16 to 22 carbon atoms of natural origin and, more particularly, mixtures thereof containing between 20 and 70% by weight of stearyl alcohol are particularly preferred.

The aqueous fatty alcohol dispersions according to the invention contain the fatty alcohols in quantities of 5 to 40% by weight and preferably in quantities of 15 to 35% by weight, based on aqueous fatty alcohol dispersions. The aqueous fatty alcohol dispersions according to the invention may additionally contain 0.5 to 10% by weight of natural and/or synthetic waxes, aliphatic $C_{14-28}$ fatty acids and/or alkali metal or amine soaps of aliphatic $C_{14-28}$ fatty acids instead of the corresponding quantities of fatty alcohol.

Natural waxes in the context of the invention are both those which are obtainable in the processing of crude oil, bitumen and/or fossils, for example the paraffin waxes and montan waxes, and also the natural esters, ketones or amides of natural $C_{16-32}$ fatty acids or of natural $C_{16-32}$ fatty alcohols, such as stearyl stearate, stearyl behenate, behenyl behenate, stearone, glycerol tristearate, glycerol tribehenate, pentaerythritol tetrastearate, hydrogenated castor oil, ethylene bis-stearamide, erucic acid amide, carnauba wax, beeswax, etc. The natural waxes and, in particular, the usual paraffin waxes with melting points according to DIN 51570 above 50° C. are particularly preferred for the purposes of the invention. Should the fatty acid component, the fatty acid soap component and/or wax be added in a corresponding quantity replacing the fatty alcohol, the minimum quantity of fatty alcohol present in the composition is at least 5% by weight and preferably at least 10% by weight.

The aqueous fatty alcohol dispersions according to the invention also contain anionic interfacially active compounds selected from the group of alcohol sulfates, ethoxylated alcohol sulfates, fatty alcohol ether sulfosuccinates and fatty alcohol ether phosphates. Particularly preferred anionic interfacially active compounds are $C_{8-18}$ fatty alcohol ether sulfates containing 6 to 100 moles of ethylene oxide and preferably 20 to 60 moles of ethylene oxide. Suitable examples of such anionic interfacially active compounds are sodium lauryl ether sulfate ethoxylated with 30 moles of ethylene oxide and sodium lauryl ether sulfate ethoxylated with 50 moles of ethylene oxide.

The aqueous fatty alcohol dispersions according to the invention contain the nonionic interfacially active compounds in quantities of 0.5 to 5% by weight and the anionic interfacially active compounds also in quantities of 0.5 to 5% by weight.

Thus, preferred aqueous fatty alcohol dispersions contain 5 to 40% by weight and preferably 15 to 35% by weight of fatty alcohols, optionally in admixture with natural and/or synthetic waxes, aliphatic $C_{14-28}$ fatty acids and/or alkali metal or amine soaps of aliphatic $C_{14-28}$ fatty acids, 0.5 to 5% by weight of anionic interfacially active compounds, 0.5 to 5% by weight of nonionic interfacially active compounds, 0 to 20% by weight of typical additives and, as the balance to 100% by weight, water.

Typical additives are protective colloids, other stabilizers or liquid fatty alcohols, fatty acids, fats, oils and silicone oils to improve the consistency of the dispersed phase without impairing its effect.

The aqueous fatty alcohol dispersions according to the invention may be prepared in known manner. Thus, the fatty alcohol may be converted into a melt and the resulting melt stirred into water, the dispersions or—occasionally—even emulsions being formed by cooling of the melt. However, the fatty alcohols may also be stirred into optionally heated water and the water subsequently heated to temperatures at which a melt is formed. Addition of the interfacially active compounds mentioned results in stabilization. There is none of the gelation which often occurs in the prior art. Where particularly fine-particle dispersions are required, they may be obtained by using a high-shear dissolver, optionally with addition of hydrocarbons liquid at room temperature, on cooling of the melt, for example in accordance with DE-A-30 01 387, or by homogenizing the pre-emulsion and subsequent cooling, for example in accordance with EP-B-399 266.

The aqueous fatty alcohol dispersions according to the invention are suitable for numerous applications because they are easy to dose and remain stable in storage. They show extremely high stability in storage, even with relatively high natural fatty alcohol contents, and retain it even at temperatures below 15° C. In addition, they are capable of suppressing or regulating foam. In another embodiment, therefore, the present invention relates to the use of the aqueous fatty alcohol dispersions described above as antifoam agents, preferably in the paper industry, in the wastewater sector, in the building industry and in the production of waterborne paints. In a particularly preferred embodiment, the aqueous fatty alcohol dispersions are used in the paper industry in aqueous systems with temperatures of at least 35° C., for example in the boiling of sulfite pulp and in the coating of paper. In papermaking, they may be used during the grinding and dispersion of paper stocks and pigments. However, the aqueous fatty alcohol dispersions described above may of course also be used anywhere where foam occurs or is to be prevented, thus in the food industry, in the building industry, in the starch industry, in the wastewater sector, particularly in sewage treatment plants, and in paints and lacquers.

In addition, it has been found that the aqueous fatty alcohol dispersions according to the invention are suitable as an additive for dispersion-bonded plasters because they prolong and thus improve the open time. In addition, the tendency of the dispersion-bonded plasters to crack is reduced where the fatty alcohol dispersions are used. A reduction in water absorption and hence an increase in the hydrophobicizing effect of the plasters are further advantages. The plasters are also easy to coat and show high permeability to water vapor so that, overall, the property spectrum of dispersion-bonded plasters can be positively influenced to a considerable extent.

EXAMPLES

A. Fatty alcohol dispersions

1) An aqueous fatty alcohol dispersion was prepared from 23% by weight of a natural $C_{18-22}$ fatty alcohol mixture containing about 50% by weight of stearyl alcohol, 4% by weight of paraffin (melting point 65° to 67° C.), 1% by weight of sodium lauryl ether sulfate ethoxylated with 30 moles of ethylene oxide (EO), 2% by weight of $C_{12/14}$ alkane epoxide ring-opened with ethylene glycol and ethoxylated with 10 moles of EO (nonionic interfacially active compound according to the invention) and 70% by weight of water. Corresponding fatty alcohol dispersions containing various nonionic interfacially active compounds known from the prior art were prepared for comparison (see Table 1).

2) An aqueous fatty alcohol dispersion was prepared from 30% by weight of a natural $C_{16-8}$ fatty alcohol mixture containing around 60 to 70% by weight of stearyl alcohol, 0.25% by weight of sodium lauryl ether sulfate ethoxylated with 30 moles of EO, 0.5% by weight of $C_{12/14}$ alkane epoxide ring-opened with ethylene glycol and ethoxylated with 10 moles of EO and 69.25% by weight of water. A corresponding fatty alcohol dispersion containing 0.5% by weight of nonylphenol with 25 mole-% of EO instead of the nonionic interfacially active compound according to the invention was prepared for comparison.

B. Use as an antifoam dispersion

The fatty alcohol dispersions containing the various nonionic interfacially active compounds prepared in accordance with Example A.1) were added in quantities of 150 µl to 1 liter of 7.5% by weight calcium lignin sulfonate solution which had been heated to 50° C. The solution was continuously stirred at 1000 r.p.m. in a glass apparatus, 600 l of air being introduced per hour. The time (in seconds) after which the solution together with the foam formed occupied a volume of 4.5 l was measured. The antifoam dispersion is more effective, the longer the time required to reach the total volume of 4.5 l. The test results are set out in Table 1. In addition, stability in storage was investigated at room temperature. To this end, the aqueous fatty alcohol dispersions containing the various nonionic interfacially active compounds were stored at room temperature. The time for which stability in storage is guaranteed, i.e. the time elapsing before gelation or creaming occurs, is shown in Table 1.

C. Stability in storage

The fatty alcohol dispersions described in A.2) were stored below 15° C. The fatty alcohol dispersions according to the invention were unchanged even after 4 months. The fatty alcohol dispersions to which nonylphenol containing 25 mole-% of EO had been added showed gelation after at most 3 days.

TABLE 1

| Fatty Alcohol Dispersion Containing | 2% By Weight of $C_{12/14}$ Epoxide Containing 10 Mole-% of Ethylene Oxide Ring Opened with Ethylene Glycol | 2% By Weight* of Isotridecanol Containing 17 Mole-% of Ethylene Oxide | 2% By Weight* of Nonylphenol Containing 25 Mole-% of Ethylene Oxide |
|---|---|---|---|
| Defoaming test B) | >100 secs. | >100 secs. | >100 secs. |
| Stability in storage at RT | >6 Months | Max. 3 months | Max. 3 months |
| Consistency after 3 months' storage at RT | Liquid < 1000 mPa · s | Highly viscous/solid | Highly viscous/solid |

*Comparison

What is claimed is:

1. An aqueous, storage stable fatty alcohol dispersion comprising:
   (a) 5% to 40% by weight of a $C_{10}$–$C_{28}$ fatty alcohol;
   (b) 0.5% to 5% by weight of anionic interfacially active compounds selected from the group consisting of alcohol sulfates, ethoxylated alcohol sulfates, fatty alcohol ether sulfosuccinates, and fatty alcohol ether phosphates;
   (c) 0.5% to 5% by weight of nonionic interfacially active compounds consisting of the reaction products of ethylene oxide with alkane-1,2-diols containing 6 to 18 carbon atoms, and
   (d) the balance, water.

2. An aqueous fatty alcohol dispersion as in claim 1 wherein said nonionic interfacially active compounds correspond to general formula (I):

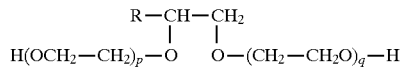  (I)

in which R is a saturated or unsaturated radical containing 6 to 18 carbon atoms attached via carbon, p and q are numbers of 0 to 50, and the sum of p and q is in the range from 5 to 50.

3. An aqueous fatty alcohol dispersion as in claim 1 wherein said fatty alcohol has a melting point above 40° C.

4. An aqueous fatty alcohol dispersion as in claims 1 wherein said fatty alcohol is saturated and contains 16 to 22 carbon atoms.

5. An aqueous fatty alcohol dispersion as in claim 1 containing 15% to 35% by weight of said fatty alcohol.

6. An aqueous fatty alcohol dispersion as in claim 1 wherein further from 0.5% to 10% by weight of said fatty alcohol has been replaced by a corresponding quantity of natural or synthetic waxes, aliphatic $C_{14\text{-}28}$ fatty acids or alkali metal or amine soaps of said aliphatic $C_{14\text{-}28}$ fatty acids; wherein the fatty alcohol component maintains a minimum quantity in the composition of at least 5% by weight.

7. The process of defoaming a foam-generating system comprising adding to said system a defoaming effective amount of an aqueous, storage stable fatty alcohol dispersion comprising:
   (a) 5% to 40% by weight of a $C_{10}$–$C_{28}$ fatty alcohol;
   (b) 0.5% to 5% by weight of anionic interfacially active compounds selected from the group consisting of alcohol sulfates, ethoxylated alcohol sulfates, fatty alcohol ether sulfosuccinates, and fatty alcohol ether phosphates;
   (c) 0.5% to 5% by weight of nonionic interfacially active compounds consisting of the reaction products of ethylene oxide with alkane-1,2-diols containing 6 to 18 carbon atoms, and (d) the balance, water.

8. A process as in claim 7 wherein said nonionic interfacially active compounds correspond to general formula (I):

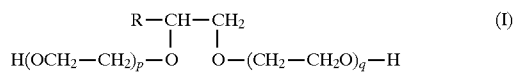  (I)

in which R is a saturated or unsaturated radical containing 6 to 18 carbon atoms attached via carbon, p and q are numbers of 0 to 50, and the sum of p and q is in the range from 5 to 50.

9. A process as in claim 7 wherein said fatty alcohol has a melting point above 40° C.

10. A process as in claim 7 wherein said fatty alcohol is saturated and contains 16 to 22 carbon atoms.

11. A process as in claim 7 wherein said aqueous fatty alcohol dispersion contains 15% to 35% by weight of said fatty alcohol.

12. A process as in claim 7 wherein further from 0.5% to 10% by weight of said fatty alcohol has been replaced by a corresponding quantity of natural or synthetic waxes, aliphatic $C_{14\text{-}28}$ fatty acids or alkali metal or amine soaps of said aliphatic $C_{14\text{-}28}$ fatty acids; wherein the fatty alcohol component maintains a minimum quantity in the composition of at least 5% by weight.

13. A process as in claim 7 wherein said foam-generating system is a paper-manufacturing system.

14. A process as in claim 7 wherein said foam-generating system is a wastewater system.

15. A process as in claim 7 wherein said foam-generating system is a paint manufacturing system.

16. A process as in claim wherein said foam-generating system is a building materials manufacturing system.

* * * * *